US006997901B2

(12) United States Patent
    Popovsky

(10) Patent No.: US 6,997,901 B2
(45) Date of Patent: Feb. 14, 2006

(54) SINGLE-USE SYRINGE

(75) Inventor: Frank Popovsky, Tahmoor (AU)

(73) Assignee: bioMD Limited, Perth (AU)

( * ) Notice: Subject to any disclaimer, the term of this patent is extended or adjusted under 35 U.S.C. 154(b) by 0 days.

(21) Appl. No.: 10/206,868

(22) Filed: Jul. 26, 2002

(65) Prior Publication Data

US 2002/0193737 A1  Dec. 19, 2002

Related U.S. Application Data

(63) Continuation of application No. PCT/AU00/01027, filed on Aug. 30, 2000.

(30) Foreign Application Priority Data

Jan. 27, 2000 (AU) ................................ PQ5249
Jul. 3, 2000 (AU) ................................ PQ8484

(51) Int. Cl.
    A61M 5/32 (2006.01)
(52) U.S. Cl. ................... 604/110; 604/197; 128/919
(58) Field of Classification Search .............. 604/110, 604/198, 187, 192, 263, 171, 195, 197; 128/919
    See application file for complete search history.

(56) References Cited

U.S. PATENT DOCUMENTS

| 4,178,930 | A | * | 12/1979 | Fisher, Jr. | ................ | 604/192 |
| 4,517,978 | A | * | 5/1985 | Levin et al. | ................ | 604/136 |
| 4,820,275 | A | | 4/1989 | Haber et al. | ................ | 604/198 |
| 4,863,434 | A | | 9/1989 | Bayless | ................ | 604/198 |
| 4,894,055 | A | | 1/1990 | Sudnak | ................ | 604/198 |
| 4,966,592 | A | * | 10/1990 | Burns et al. | ................ | 604/198 |
| 4,985,021 | A | | 1/1991 | Straw et al. | ................ | 604/198 |
| 5,057,079 | A | | 10/1991 | Tiemann et al. | ............. | 604/110 |
| 5,057,086 | A | | 10/1991 | Dillard, III et al. | .......... | 604/195 |
| 5,092,851 | A | | 3/1992 | Ragner | ................ | 604/192 |
| 5,201,720 | A | | 4/1993 | Borgia et al. | ................ | 604/198 |
| 5,215,534 | A | | 6/1993 | De Harde et al. | .......... | 604/198 |

(Continued)

FOREIGN PATENT DOCUMENTS

EP    0 680 767 A1    11/1995

(Continued)

OTHER PUBLICATIONS

"Supplemental European Search Report for EP 00 95 5961", (Apr. 11, 2003),1.

(Continued)

Primary Examiner—Nicholas D. Lucchesi
Assistant Examiner—Matthew F. DeSanto
(74) Attorney, Agent, or Firm—Schwegman, Lundberg, Woessner & Kluth, P.A.

(57) ABSTRACT

A single use syringe (10) includes a needle (18), barrel (16), plunger assembly (20) and shield (12). The barrel (16) bears a locking member (26) which encircles the front end of the barrel (16) and is carried forward by the barrel (16) to a position where it engages the shield (12) and is retained by the shield (12) such that the locking member (26) is separated from the barrel (16) as the barrel (16) is withdrawn rearwardly after use. The locking member (26) is resilient and, after it is removed from the barrel (16), assumes a configuration which prevents subsequent forward movement of the barrel (16) within the shield (12). The barrel includes a frangible seal (30) which is broken by rearward movement of needle mount (32). The shield (12) includes a shield extender (14) for controlling the depth of penetration of the needle. The syringe can also be used to inject medicament into a IV bag via a male port as shown in FIG. 7.

19 Claims, 4 Drawing Sheets

U.S. PATENT DOCUMENTS

| | | | |
|---|---|---|---|
| 5,215,535 A | 6/1993 | Gettig et al. | 604/198 |
| 5,222,945 A | 6/1993 | Basnight | 604/198 |
| 5,259,841 A | 11/1993 | Hohendorf et al. | 604/110 |
| 5,269,761 A | 12/1993 | Stehrenberger et al. | 604/110 |
| 5,273,541 A | 12/1993 | Malenchek | 604/110 |
| 5,290,256 A | 3/1994 | Weatherford et al. | 604/198 |
| 5,312,372 A | 5/1994 | DeHarde et al. | 604/198 |
| 5,342,309 A | 8/1994 | Hausser et al. | 604/110 |
| 5,360,408 A | 11/1994 | Vaillancourt | 604/198 |
| 5,368,577 A | 11/1994 | Teoh et al. | 604/198 |
| 5,425,721 A | 6/1995 | Malenchek | 604/198 |
| 5,437,639 A | 8/1995 | Malenchek | 604/110 |
| 5,478,314 A | 12/1995 | Malenchek | 604/110 |
| 5,492,536 A | 2/1996 | Mascia | 604/197 |
| 5,527,284 A | 6/1996 | Ohnemus et al. | 604/110 |
| 5,562,624 A * | 10/1996 | Righi et al. | 604/263 |
| 5,562,626 A * | 10/1996 | Sanpietro | 604/263 |
| 5,584,818 A | 12/1996 | Morrison | 604/197 |
| 5,591,138 A | 1/1997 | Vaillancourt | 604/263 |
| 5,681,291 A | 10/1997 | Galli | 604/192 |
| 5,944,700 A * | 8/1999 | Nguyen et al. | 604/263 |
| 5,980,494 A * | 11/1999 | Malenchek et al. | 604/198 |
| 6,099,503 A | 8/2000 | Stradella | 604/135 |
| 6,099,504 A | 8/2000 | Gross et al. | 604/140 |
| 6,206,853 B1 | 3/2001 | Bonnet | |
| 6,419,658 B1 * | 7/2002 | Restelli et al. | 604/198 |
| 6,527,742 B1 | 3/2003 | Malenchek | 604/110 |
| 2004/0204678 A1 | 10/2004 | Popovsky | |
| 2004/0236281 A1 | 11/2004 | Popovsky | |

FOREIGN PATENT DOCUMENTS

| | | | |
|---|---|---|---|
| EP | WO 99/37345 | * | 7/1999 |
| WO | WO-93/00949 | | 1/1993 |
| WO | WO-95/26764 A1 | | 10/1995 |
| WO | WO-98/35714 | | 8/1998 |
| WO | WO-98/56437 | | 12/1998 |
| WO | WO-98/56442 A1 | | 12/1998 |

OTHER PUBLICATIONS

"European Search Report for EP Application No. 04 07 6405, dated Jul. 28, 2004, 2 pgs",.

* cited by examiner

SINGLE-USE SYRINGE

RELATED APPLICATIONS

This application is a continuation under 35 U.S.C. 1.111 (a) of International Application No. PCT/AU00/01027 filed Aug. 30, 2000 and published in English as WO 01/54758 A1 on Aug. 2, 2001, which claimed priority from Australian Applications PQ 5249 filed Jan. 27, 2000, and PQ 8484 filed Jul. 3, 2000, which applications and publication are incorporated herein by reference.

FIELD OF INVENTION

The present invention relates to single-use syringes.

BACKGROUND OF THE INVENTION

In recent times there has been a proliferation of single-use syringe designs which incorporate shields that can be moved to a forward position to shield the needle after use. In most instances, the shield is locked in the forward position after use to prevent multiple uses of the syringe and/or to prevent inadvertent needle-stick injury.

Examples of syringe designs incorporating shields can be found in U.S. Pat. No. 5,584,818 to Morrison, U.S. Pat. No. 5,492,536 to Mascia, U.S. Pat. No. 5,527,294 to Weatherford, U.S. Pat. No. 5,591,138 to Vaillancourt, U.S. Pat. No. 6,099,504 to Gross, U.S. Pat. No. 4,820,275 to Haber, U.S. Pat. No. 5,269,761 to Stehrenberger, U.S. Pat. No. 5,562,626 to Sanpietro, U.S. Pat. No. 4,863,434 to Bayless, U.S. Pat. No. 4,985,021 to Straw, U.S. Pat. No. 5,057,079 to Tiemann, U.S. Pat. No. 5,057,086 to Dillard, U.S. Pat. No. 5,092,851 to Ragner, U.S. Pat. No. 5,201,720 to Borgia, U.S. Pat. No. 5,215,534 to De Harde, U.S. Pat. No. 5,215,535 to Gettig, U.S. Pat. No. 5,222,945 to Basnight, U.S. Pat. No. 5,290,256 to Weatherford, U.S. Pat. No. 5,312,372 to De Harde, and U.S. Pat. No. 5,360,408 to Vaillancourt.

Most of these shielded-syringe designs are provided to the user with the shield in the retracted position and thus some triggering or manual manipulation of the shield is required to release the shield to the forward position after use. In many designs, the movement of the shield to the forward position after use is assisted by a spring.

Only a few of these known designs are provided to the user with the shield initially in the forward position. In these cases, it is necessary for the user to manipulate some form of release mechanism to enable the shield to be moved to the rearward position to expose the needle for use, and after use it is again necessary to manipulate some form of release mechanism to release the shield to the forward position. Again, many of these designs incorporate a spring which biases the shield to the forward position.

SUMMARY OF INVENTION

According to one aspect the invention resides in a single-use syringe which is provided to the user with the shield in a forward position, yet requires no manual manipulation of release mechanisms or the like to release the shield to the rearward position for use, nor further manual manipulation to release and lock the shield in the forward position after use.

The above ergonomic advantages are achieved by a single-use syringe as defined in the attached claims.

BRIEF DESCRIPTION OF THE DRAWINGS

The invention will now be described with reference to an example for illustrative purposes and wherein.

DETAILED DESCRIPTION

Figure 1:
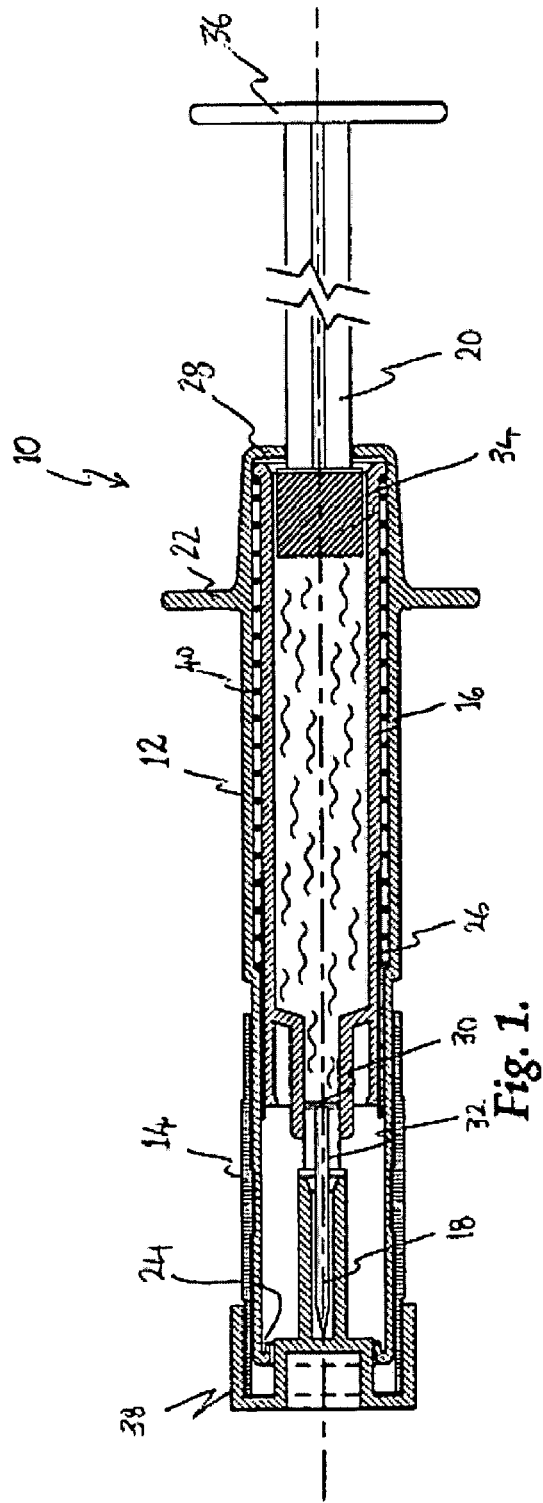
FIGS. 1 to 6 are a series of sequential longitudinal sectioned views of a single-use syringe demonstrating operation of the single-use syringe.

Referring firstly to FIG. 1, there is illustrated a pre-filled single-use syringe 10 including a shield 12 having a shield extender 14, a barrel 16 mounted for reciprocation within the shield 12 and having a needle 18 at its forward end, and a plunger assembly 20 mounted for reciprocation within the barrel 16.

The shield 12 is generally cylindrical in shape and includes a generally cylindrical shield extender 14 at its forward end. The shield extender 14 can be selectively extended to control the depth of penetration of the needle during use as will be described in more detail later. Conventional finger receiving portions 22 are defined towards the rear end of the shield 12, the finger receiving portions 22 adapted to receive a user's fingers in the conventional manner during use. The forward end of the shield includes a circular slot 24 which engages and retains a locking member 26 during use as will be described later. The rearward end of the shield includes a rear collar flange 28 which limits the barrel's 16 rearward travel within the shield 12.

The barrel 16 is pre-filled with medicament and is sealed at its rearward end by the plunger assembly 20 and at the forward end by a frangible seal 30 which can be broken by the needle mount 32 prior to use as will be discussed later. The needle 18 extends forwardly from the needle mount 32 which is itself located immediately forward of the frangible seal 30. The barrel 16 bears a generally cylindrical bifurcated locking member 26 about its forward end which is adapted to engage and be retained by the circular slot 24 in the shield 12 as will be described in greater detail later.

The plunger assembly 20 is conventional in construction and includes a piston 34 at its forward end which sealingly engages the internal bore of the barrel 16.

The plunger assembly 20 also defines a conventional thumb engaging portion 36 at its rearward end.

Referring firstly to FIG. 1 there is illustrated a pre-filled single-use syringe in the form in which it would be supplied to a user. Normally, the pre-filled single-use syringe 10 would be individually packaged and supplied in a sterile plastic package which is not illustrated. Both the packaging and syringe itself would identify the medicament and volume of medicament present in the barrel of the syringe.

As mentioned above, the medicament is sealed within the barrel 16 by the piston 34 of the plunger assembly 20 at the rearward end of the barrel 16 and by a frangible seal 30 at the forward end of the barrel 16.

Figure 2:
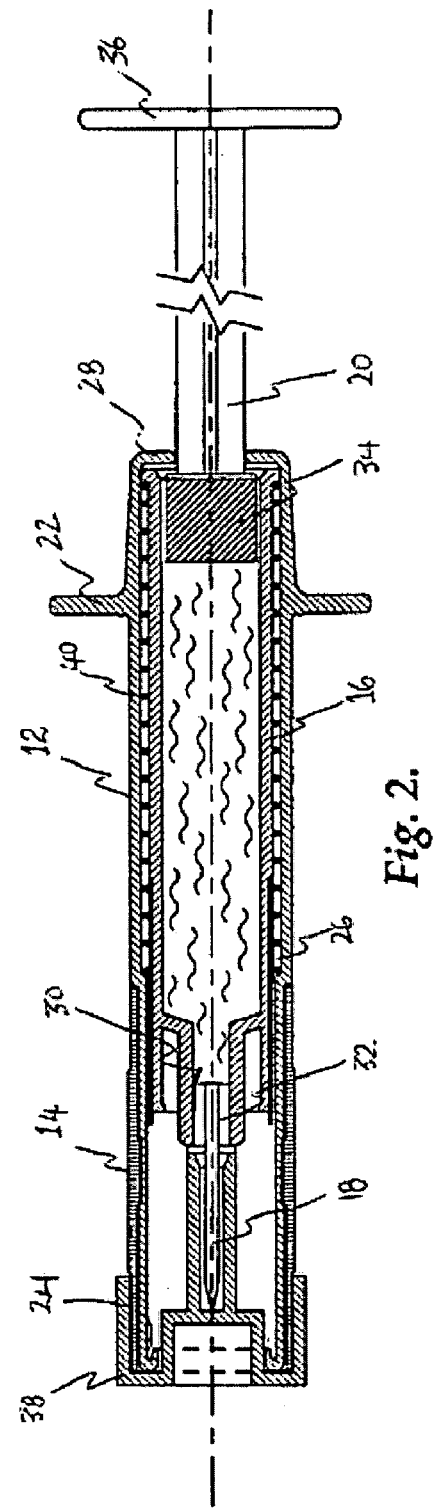

The first step in the use of the syringe is the breaking of the frangible seal 30 and this is best understood with comparative reference to FIGS. 1 and 2.

Shield extender 14 is mounted via a coarse screw thread on the forward end of shield 12 such that rotation of shield extender 14 relative to shield 12 causes the shield extender to reciprocate in the forward or aft direction relative to shield 12.

As can be seen with reference to FIG. 1, the syringe is provided with the shield extender 14 in a slightly forward position, i.e. the shield extender 14 extends slightly forward beyond the forward-most extent of the shield 12.

A cap 38 is provided, and the cap 38 has an outer skirt which is frictionally seated on the shield extender 14 as shown. The shield extender 14 also has a small outwardly extending shoulder which is engaged by the outer skirt and prevents rearward movement of the cap 38 relative to the shield extender 14. The cap 38 also encloses the needle 18 with a rearwardly extending inner skirt which seats on the tapered forward end of the needle mount 32 as shown.

With reference now to FIG. 2, the cap 38 and shield extender 14 have been rotated relative to shield 12 such that the shield extender 14 and cap have moved in unison rearwardly relative to shield 12 until the rear end of the shield extender 14 has abutted a small outwardly extending shoulder formed on the shield 12 which prevents further rearward movement of the shield extender 14 relative to the shield 12. Simultaneously, the needle mount 32 has been driven rearwardly by the inner skirt of the cap 38 such the frangible seal 30 has been broken and the needle 18 is thus now in fluid communication with the interior of the barrel 16. The frangible seal 30 is designed to have a portion of its circumference form a "live" or integral hinge about which the remainder of the frangible seal 30 pivots. A frangible seal and live hinge per se is known from PCT/AU99/00422.

It will be noted that the needle mount 32 is non-conventional in construction in that it is cylindrical and fully contained within the seal-containing bore of the spigot-shaped nose of the barrel 16. In contrast, conventional needle mounts include a rearwardly projecting skirt which surrounds the exterior of the spigot-shaped nose of the barrel 16. It is for this reason that the syringe disclosed in PCT/AU99/00422 utilised a cylindrical tube 21 intermediate the conventional needle mount 7 and frangible seal 9 for the purpose of breaking the frangible seal 9.

Figure 3:
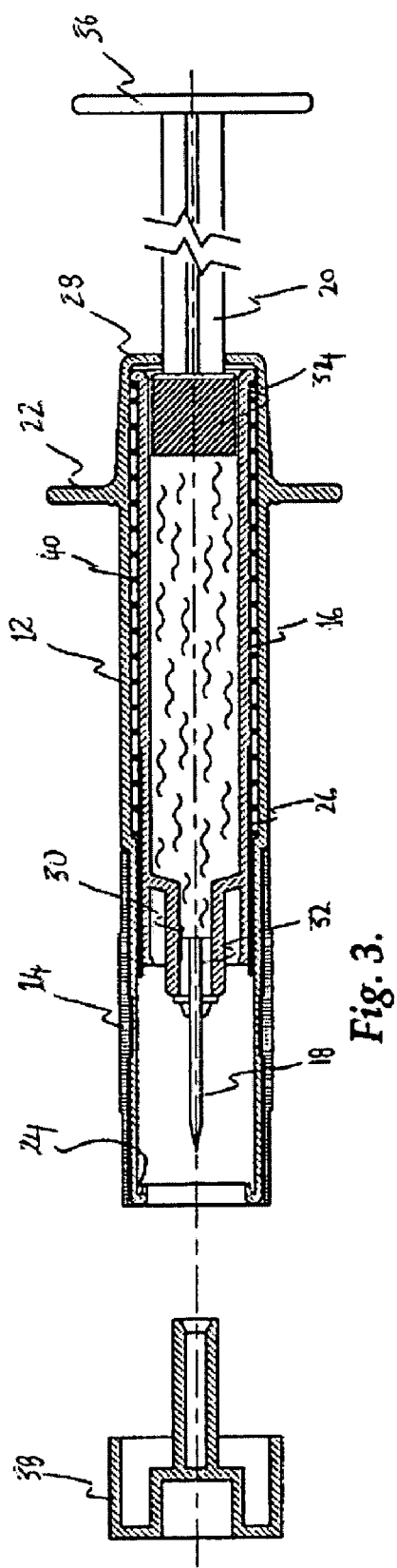

With reference to FIG. 3, cap 38 has been removed and the needle is now ready for use with the needle being shielded, but in fluid communication with the interior of the barrel 16 which accommodates the medicament.

Figure 3A:
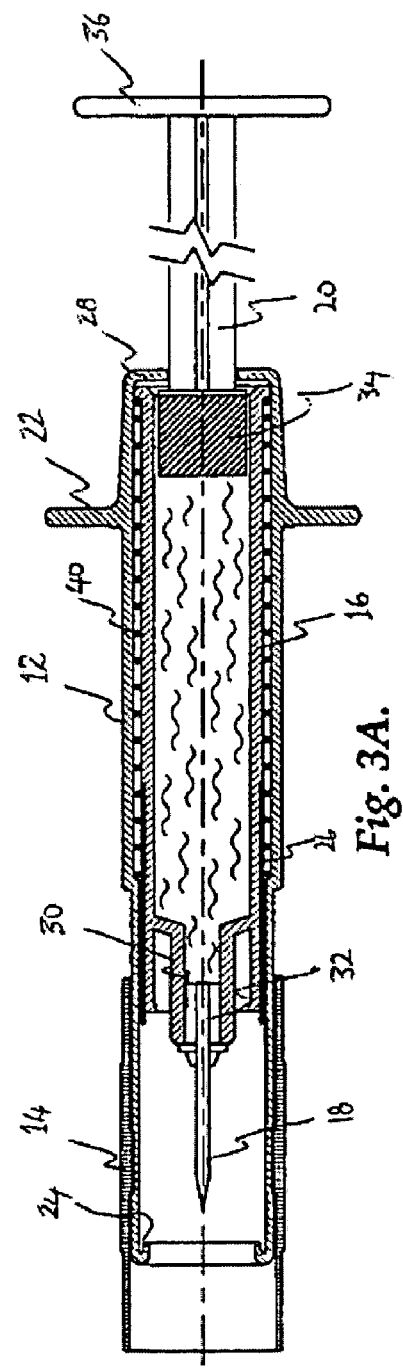

Referring to FIG. 3A, the shield extender 14 has been rotated in the reverse direction relative to the shield 12 such that the shield extender 14 has moved forwardly relative to shield 12 from its fully retracted position and it now extends forwardly beyond the forward-most extent of shield 12. Selective rotation of shield extender 14 relative to shield 12 allows the user to control the depth of penetration of the needle 18 during use. The further the shield extender 14 is extended beyond the shield 12, the shallower the penetration of the needle 18 in the patient.

Figure 4:
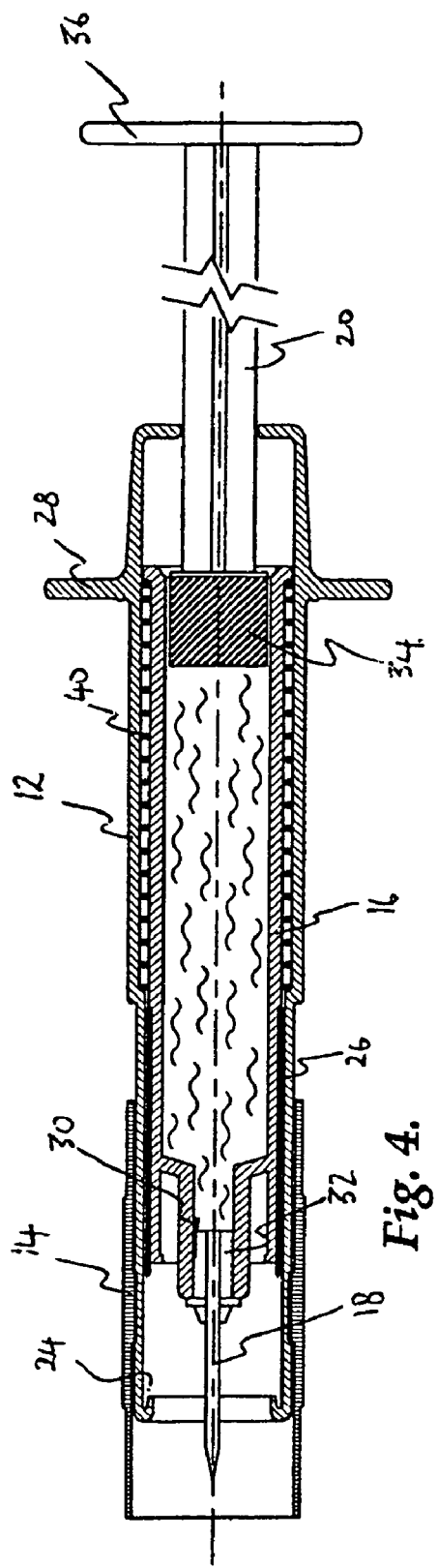

With reference now to FIG. 4, the user has begun squeezing together thumb receiving portion 36 of the plunger assembly 20 and finger-receiving portions 22 of the shield 12 in the conventional manner thereby compressing compression spring 40 which is provided between a small outwardly extending shoulder formed on the rear end of barrel 16 and a small inwardly directed shoulder formed midway along the length of shield 12.

As shown in FIG. 4, the plunger assembly 20 has not yet moved forwardly relative to barrel 16 to express medicament from the needle 18. Rather, plunger assembly 20 and barrel 16 have moved forwardly in unison within shield 12 and shield extender 14. Plunger assembly 20 and barrel 16 will continue to move forward in unison until the forward end of barrel 16 engages the forward end of shield 12 whereat the compression spring 40 reaches its maximum compression.

Figure 5:
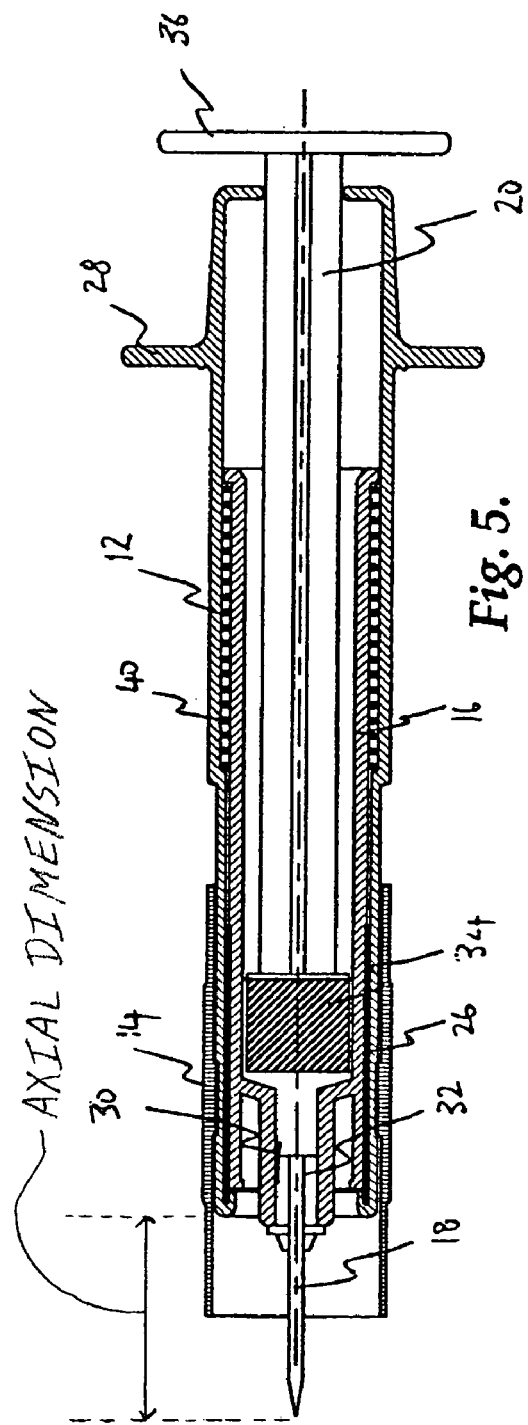

With reference now to FIG. 5, the barrel 16 has moved to the fully forward position relative to shield 12 such that the forward end of barrel 16 engages the forward end of shield 12 and the needle 18 is maximally exposed. Thereafter, any further squeezing together of the thumb receiving portion 36 and finger receiving portions 22 in the conventional manner causes the plunger assembly 20 to move forward relative to barrel 16 thereby expressing the medicament from the interior of the barrel 16.

With reference to FIG. 5, it should be noted that the forward end of locking member 26 (which has been carried forward on the forward end of barrel 16) has engaged the circular slot 24 defined in the forward end of shield 12. The locking member 26 is thereafter retained in this position by virtue of its engagement with the slot 24.

Figure 6:
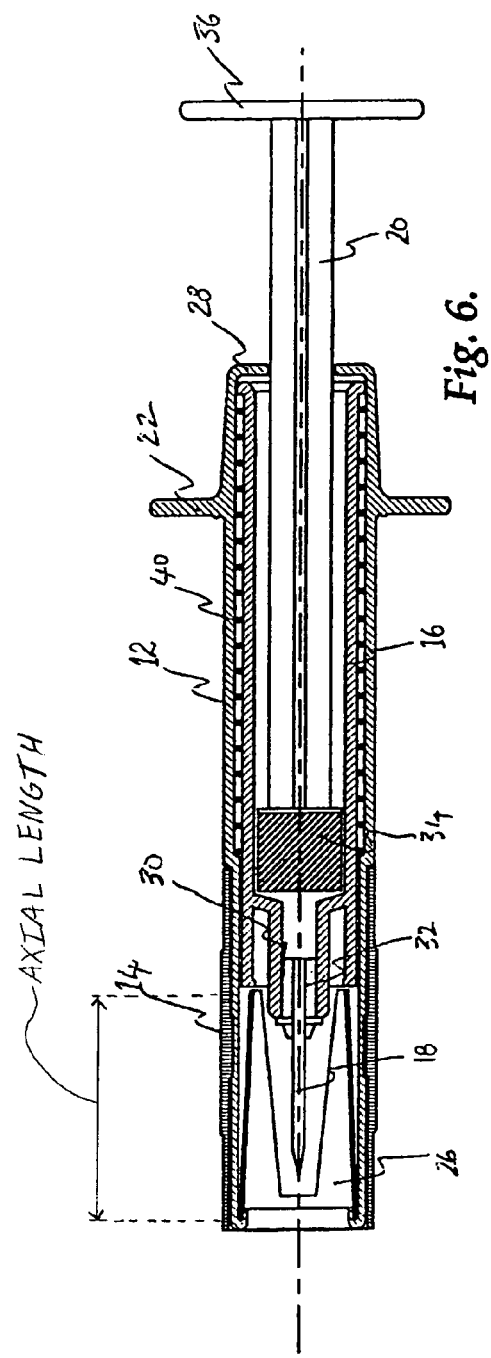

With reference to FIG. 6, the squeezing force applied by the user has been discontinued and the barrel 16 and plunger assembly 20 have moved rearwardly in unison under the influence of compression spring 20. It will be noted that locking member 26 is retained in the circular slot 24 defined in the forward end of shield 12. As barrel 16 moves rearwardly relative to shield 12, locking member 26 slides or is pulled off the forward end of barrel 16 until it is fully clear of barrel 16 as shown in FIG. 6. At this stage, the rear end of locking member 26, which is formed of a resilient plastics material having a memory, snaps inwardly to adopt a truncated and bifurcated cone-like shape as shown in FIG. 6. Of course, previously whilst the locking member 26 was encircling barrel 16, it adopted a bifurcated cylindrical shape. Thus, the resilient memory of the locking member 26 causes the locking member to change shape from a generally cylindrical shape to a generally truncated cone-like shape when it is "pulled" off the forward end of the barrel 16 via its engagement with slot 24.

Once the locking member 26 has adopted the truncated cone-like shape as shown in FIG. 6, subsequent forward movement of the barrel 16 relative to the shield 12 is prevented by virtue of physical interference with the locking member 26 and hence the locking member 26 prevents subsequent unshielding of the needle 18.

Figure 7:
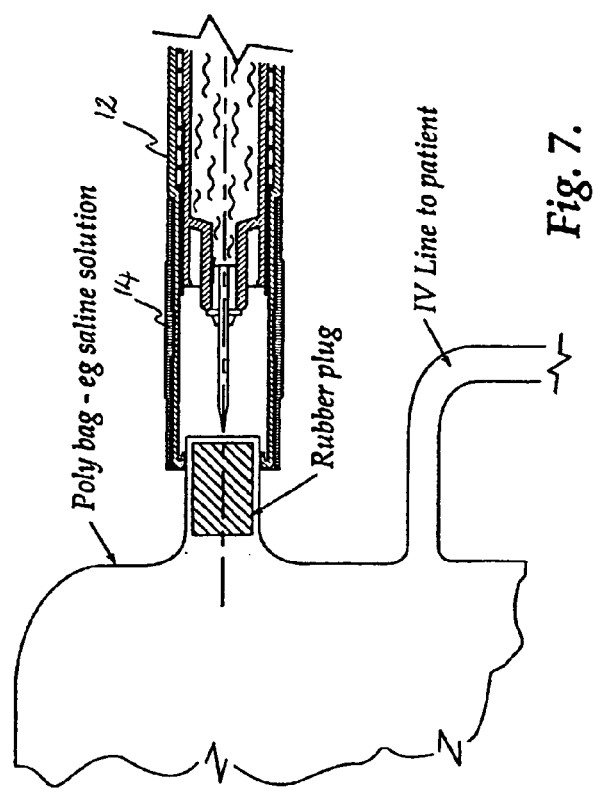
FIG. 7 shows the single-use syringe engaging the male port of an IV fluid bag.

Referring to FIG. 7, the single-use syringe can also be conveniently used in a safe manner with intravenous polybags as shown. In this regard, the forward end of the shield 12 is sized so as to closely receive the male port of a polybag as shown. Typically, these male ports are sealed by a rubber plug as shown. The needle can penetrate through the rubber plug and the medicament can then be injected into the polybag for IV feed to the patient via an established catheter or the like. After injection of the medicament into the polybag, the needle is withdrawn and the rubber plug is sufficiently resilient to be reseal the male port of the poly bag.

The present invention provides a single-use syringe which is supplied to the user with the shield in the forward or shielding position, yet requires no non-conventional manipulation or activation of release mechanisms or the like to move the shield back to the needle-exposed position for use. Furthermore, no non-conventional manipulation of release mechanisms or the like is required to release the shield to the forward protective position after use. The user simply squeezes their thumb and fingers together in the conventional manner and this single, conventional action exposes the needle 18, activates the locking member 26 via its engagement with the slot 24, and expresses the medicament. Discontinuation of the squeezing force cause the shield to return to its forward or protective position under spring bias whereat it is locked to prevent subsequent use or inadvertent needle-stick injuries.

It will of course be realised that whilst the above has been given by way of an illustrative example of this invention, all such and other modifications and variations hereto, as would be apparent to persons skilled in the art, are deemed to fall within the broad scope and ambit of this invention as is herein set forth.

What is claimed is:

1. A single-use syringe comprising:
   a shield having a forward end;
   a barrel having a needle at its forward end, the needle having a forward end, the barrel being mounted for axial reciprocation within the shield between a rearward position whereat the needle is shielded and a forward position of the barrel whereat the forward end of the needle extends beyond the forward end of the shield by an axial direction, wherein the barrel is initially in the rearward position with the needle being shielded by the shield; and
   a locking member mounted on the barrel, and the barrel carries forward the locking member when the barrel is moved from the initial rearward position to the forward position, and wherein the locking member engages the shield at the forward position, and is dismounted from the barrel and is retained in a forward position by the shield as the barrel is returned to the rearward position, the dismounted locking member preventing subsequent forward movement of the barrel, and wherein the dismounted locking member has an axial length greater than the axial dimension between the forward end of the needle and the forward end of the shield when the barrel is in the forward position.

2. A single-use syringe as claimed in claim 1, wherein the barrel is biased to the rearward position.

3. A single-use syringe as claimed in claim 2, wherein the syringe includes a plunger assembly mounted for axial reciprocation within the barrel, and wherein the plunger assembly defines a thumb receiving portion and the shield defines at least one finger receiving portion such that the thumb and finger(s) of a single hand of a user can engage the syringe to firstly move the barrel forward relative to the shield to expose the needle, and thereafter to move the plunger assembly forward relative to the barrel to express medicament.

4. A single-use syringe as claimed in claim 1, wherein the locking member initially encircles the forward end of the barrel, and wherein the locking member prevents subsequent forward movement of the barrel when it is removed from the forward end of the barrel.

5. A single-use syringe as claimed in claim 4, wherein the locking member is a bifurcated cylinder which adopts a truncated cone-like shape when it is removed from the forward end of the barrel.

6. The single-use syringe of claim 1, wherein the barrel includes a biasing member adapted to bias the barrel into the rearward position, and the biasing member is enclosed with the shield.

7. The single-use syringe of claim 6, wherein the biasing member is a compression spring.

8. A single-use syringe as claimed in claim 1, wherein the syringe includes a plunger assembly mounted for axial reciprocation within the barrel, and wherein the plunger assembly defines a thumb receiving portion and the shield defines at least one finger receiving portion such that the thumb and finger(s) of a single hand of a user can engage the syringe to firstly move the barrel forward relative to the shield to expose the needle, and thereafter to move the plunger assembly forward relative to the barrel to express medicament.

9. A single-use syringe as claimed in claim 1, wherein the locking member engages, and is retained by, a slot defined in the shield.

10. A single-use syringe as claimed in claim 1, wherein the shield includes a shield extender for controlling the depth of penetration of a needle.

11. A single-use syringe as claimed in claim 1, wherein the forward end of the shield is adapted to receive the male port of an IV bag.

12. The single-use syringe of claim 1, wherein the shield includes a circular slot adapted to engage the locking member and retain the locking member once engaged.

13. The single-use syringe of claim 1, wherein the barrel is pre-filled with medicament and includes a forward end having a frangible seal.

14. The single-use syringe of claim 1, wherein the locking member is free from direct manual manipulation whereby the barrel moves from the initial rearward position to the forward position and the shield is locked by the locking member in the forward position after the barrel returns to the rearward position.

15. The single-use syringe of claim 1, wherein the shield includes a shield extender at a forward end, and wherein the needle is free from the shield extender only when the needle contacts a patient.

16. The single-use syringe of claim 1, wherein the shield is engaged by a user and remains fixed, and wherein the barrel and needle move relative to the shield to deliver medicament and shield the needle.

17. The single-use syringe of claim 1, wherein the locking member is a bifurcated cylinder which adopts a truncated cone-like shape when it is removed from the forward end of the barrel.

18. A single-use syringe, comprising:
   a shield;
   a barrel being mounted for axial reciprocation within the shield and having a forward end;
   a needle extending the forward end of the barrel;
   a locking member adapted to engage the forward end of the barrel;
   a medicament-expressing position with the needle exposed from the shield; and
   a protective position subsequent to the medicament-expressing position with the needle again shielded by the shield and the locking member fixing the barrel in a retracted position with the needle fixed within the shield, wherein the barrel is adapted to store medicament,
   wherein the barrel is adapted to move within the shield from an initial position to the medicament-expressing position and then to the protective position,
   wherein the locking member engages the shield at the medicament-expressing position and is retained in a forward position by the shield as the barrel is returned to the protective position, and
   wherein the locking member prevents subsequent forward movement of the barrel so as to fix the needle within the shield, wherein the locking member includes a bifurcated cylinder which adopts a truncated cone-like shape when it is removed from the forward end of the barrel,
   wherein the shield includes a forward end and a slot at the forward end thereof, and wherein the locking member engages and is retained by the slot, wherein the barrel includes a frangible seal between the medicament and the needle, wherein the shield includes a shield extender adapted to control the depth of penetration of the needle and adapted to cause the frangible seal to be broken.

19. The single-use syringe of claim 18, wherein the slot is circular.

* * * * *